United States Patent [19]
Vert et al.

[11] Patent Number: 5,567,431
[45] Date of Patent: Oct. 22, 1996

[54] POLYLACTIC ACID-BASED IMPLANT SUSCEPTIBLE OF BIORESORPTION CONTAINING AND ANTIBIOTIC

[75] Inventors: Michel Vert, Mont-Saint-Aignan; Jacques Mauduit, Bacqueville En Caux, both of France; Niels Bukh, Hellerup, Denmark

[73] Assignee: Centre National de la Recherche Scientifique (CNRS), Paris, France

[21] Appl. No.: 117,185

[22] PCT Filed: Mar. 13, 1992

[86] PCT No.: PCT/FR92/00231

§ 371 Date: Dec. 8, 1993

§ 102(e) Date: Dec. 8, 1993

[87] PCT Pub. No.: WO92/16193

PCT Pub. Date: Oct. 1, 1992

[30] Foreign Application Priority Data

Mar. 14, 1991 [FR] France ................... 91 03110

[51] Int. Cl.⁶ .............. A61F 2/02; A61K 9/14; A61K 9/50; A61K 47/32
[52] U.S. Cl. ............ 424/426; 424/489; 424/501; 514/772.3; 514/963; 514/965
[58] Field of Search .................. 424/423, 426, 424/489, 501; 514/772.3, 963, 965

[56] References Cited

U.S. PATENT DOCUMENTS

| | | | |
|---|---|---|---|
| 4,719,246 | 1/1988 | Murdoch et al. | 521/134 |
| 5,180,765 | 1/1993 | Sinclair | 524/306 |

FOREIGN PATENT DOCUMENTS

| | | |
|---|---|---|
| 0049068 | 4/1982 | European Pat. Off. . |
| 0251680 | 1/1988 | European Pat. Off. . |
| 0251680 | 1/1988 | European Pat. Off. . |
| 0374531 | 6/1990 | European Pat. Off. . |
| 3444832 | 6/1985 | Germany . |
| 2091554 | 8/1982 | United Kingdom . |
| 9015586 | 12/1990 | WIPO . |

*Primary Examiner*—Carlos Azpuru
*Attorney, Agent, or Firm*—Cushman Darby & Cushman L.L.P.

[57] ABSTRACT

Implantable poly(lactic acid)-based pharmaceutical composition which comprises at least one water soluble antibiotic in particle form with controlled dimensions, less than 100 µm uniformly dispersed in an amorphous poly(lactic acid) matrix, said composition being in ground powder or thin film form. Application especially in initiating local internal antibiotic therapy by the gradual release of the antibiotic substance.

21 Claims, No Drawings

POLYLACTIC ACID-BASED IMPLANT SUSCEPTIBLE OF BIORESORPTION CONTAINING AND ANTIBIOTIC

The subject of the present invention is an implantable and bioresorbable pharmaceutical composition based on poly(lactic acid), intended especially for implementing a local internal antibiotherapy.

It is known that the pharmaceutical industry is currently looking for new implantable medicinal forms, which progressively release the active principle, with the aim of overcoming the faults of the conventional pharmaceutical forms and in particular of avoiding the necessity for repeated administrations.

Controlled-release systems are generally micro-capsules, microspheres or bulk implants of various forms, for example cylindrical forms (needles). In these systems, the active principle is generally dispersed in a bioresorbable polymer matrix.

Among bioresorbable polymers, poly(lactic acid)s are the most used. The literature provides varied examples of application of such systems, especially to anti-cancer chemotherapy and to hormonotherapy.

In the field of antibiotherapy, poly(lactic acid) microspheres containing erythromycin have already been described. These microspheres are administered by parenteral injection and act systemically, with progressive release of the antibiotic, while reducing irritation of the tissues at the point of injection; see P. K. Gupta et al., 5th Congr. Int. Technol. Pharm., 4, 73–79, 1989.

However, microspheres do not constitute a satisfactory form of administration, on the one hand because they contain residues of surface-active agents used in their preparation and, on the other hand, because they generally contain a thin polymer layer at the surface which is free of active substance, which at first delays the release of this substance.

The subject of the present invention is an implantable pharmaceutical composition intended in particular for implementing a not general, but local, antibiotherapy, essentially restricted to sites of operations, in order to prevent and/or cure local infections which must always be feared after a surgical operation.

Systemic antibiotherapy with broad-spectrum antibiotics administered parenterally is currently used to prevent these infections. The disadvantages of general antibiotherapy are known: painful injection with irritation of tissues, renal or hepatic toxicity and the necessity for repeated administrations.

The subject of the present invention is to overcome these disadvantages by making available to the surgeon a bioresorbable composition, intended to be implanted at the site of operation, before suturing the wound and making it possible to implement a local internal antibiotherapy by progressive release of the antibiotic substance. Of course, the bioresorbable composition of the invention, intended to provide a local antibiotherapy affecting the site of operation, is mainly deployed in contact with soft internal tissues accessible via the wound. It can also be placed on the contact surface between a bulk bone implant (especially osteosynthesis component) and the bone cavity intended to receive this implant.

For ease of such a use, the composition of the invention is provided in the form of a powder or thin film. The powder is a powder obtained by grinding a dispersion of the antibiotic in the polymer matrix, which makes it possible to avoid the disadvantages, indicated above, of the microspheres.

In fact, it has been discovered that compositions in the ground powder or thin film form make it possible to obtain a satisfactory release profile, with an initial phase of rapid and strong release (or "burst") of the antibiotic present at the surface, making it possible to obtain a suitable attack dose, followed by a phase of slower release of the antibiotic over a sufficiently long period of time, for example about ten days.

In the compositions of the invention, degradation of the polymer matrix is relatively slow with respect to the period of release of the antibiotic, in order that this release is controlled by dissolution/diffusion phenomena of the antibiotic in the external medium, and not as a result of the degradation of the matrix.

Another characteristic of the compositions of the invention is that the antibiotic is added in the form of particles having controlled sizes, which makes it possible to better control the reproducibility and the duration of the release phenomenon of the antibiotic.

One advantage of the compositions of the invention is that, as will be shown hereinbelow, by the choice of the molecular masses of the polymer matrix, of the concentration of the antibiotic and of the size of the particles in the case of powders, or alternatively by the combination of powders having different characteristics, it is possible to adapt and to vary the release profiles of the antibiotic as desired.

The subject of the present invention is thus an implantable and bioresorbable pharmaceutical composition based on poly(lactic acid), intended for implementing a local internal antibiotherapy, characterized in that it comprises at least one water-soluble antibiotic in the form of particles of controlled sizes, dispersed homogeneously in an amorphous poly(lactic acid) matrix, and in that the said composition is provided in the form of a ground powder or a thin film.

In the composition of the invention, the antibiotic particles are distributed homogeneously (randomly), which differentiates them from the microspheres, for example, as already indicated above.

These antibiotic particles have sizes of less than 100 μm, and in particular of between 0.01 and 50 μm.

The Applicant have discovered that an important condition for obtaining a homogeneous dispersion and a suitable release of the active substance in a poly(lactic acid) matrix is that of using an amorphous poly(lactic acid), because the semi-crystalline polymer matrices lead to excessively fast releases of the active substance and to excessively lengthy degradation times of the polymer.

For this, it is advisable to use a polymer consisting of a mixture of units derived from D- and L-lactic acids, the proportions of each of the D- and L-units being sufficient for the matrix to be amorphous. It is possible to use, in particular, amorphous poly(lactic acids) which are obtained when from 20 to 80% of the units which they contain are D-lactic units (the other units being, of course, L-lactic units). It is possible, in particular, to use polymers obtained starting from racemic modifications of D,L-lactic acid, or of D,L-lactide, in order to obtain amorphous polymers containing equal proportions of the two types of units.

Another subject of the invention is a process for the preparation of a composition as defined above. This process is characterized in that the said antibiotic particles and the said poly(lactic acid) are mixed so as to obtain a homogeneous dispersion and then in that, according to known methods, the dispersion obtained is put into the form of a ground powder or thin film.

According to a first embodiment, the composition of the invention is provided in the form of a powder obtained by grinding a homogeneous dispersion of the antibiotic in an amorphous poly(lactic acid) matrix having a molecular mass at least equal to 10,000, in particular at least equal to 30,000. In fact, polymers having an excessively low molecular mass are not suitable for being used on their own: they have a tendency to give, with the antibiotic, either pasty products or powders in which the release profiles of the antibiotic are less suitable because they lead, in particular, to an excessively fast release of the active substance.

The molecular mass of the amorphous poly(lactic acid)s used according to the invention in the manufacture of ground powders is generally between 10,000 and 200,000, and preferably between 20,000 and 300,000.

Of course, this is a mean molecular mass, measured, for example, by gel permeation chromatography in dioxane with respect to polystyrene standards.

It is known that poly(lactic acid)s of relatively high molecular masses can be obtained, in particular, by lactide polymerization, for example by polymerization of D,L-lactide. There also exist usable high molecular mass poly(lactic acid)s which are commercial products.

In order to prepare the dispersion of the antibiotic in the polymer, it is possible, for example, to mix the antibiotic particles in the polymer in a solvent of the polymer in which the antibiotic is insoluble. After obtaining a dispersion of the antibiotic in the solution of the polymer, the solvent is evaporated, for example in a rotary evaporator to promote the homogeneity of the dispersion. The mass obtained is then ground, so as to obtain a powder having, for example, particle sizes between 0.1 and 1 mm.

By virtue of this process, in which dissolution followed by reprecipitation of the antibiotic is avoided, it is possible to control the sizes of the antibiotic particles in the powders obtained.

The ground powder obtained can then, if desired, be sieved to obtain powders having the desired particle size.

Liberation studies of the antibiotic substance, in an isotonic phosphate buffer of pH 7.4 at 37° C. have shown that the rate of release of the antibiotic increases when the sizes of the particles of the composition decreases. It is optionally possible to benefit from this phenomenon by using a mixture of at least two sets of particles having different mean sizes. The small particles will make possible the rapid release of an attack dosage of the antibiotic, whereas the bigger particles will give a sustained release of antibiotic. For example, a mixture of particles having sizes of 0.1 to 0.2 mm with particles having mean sizes of 0.5 to 1 mm, in suitable proportions, will be used.

The liberation studies have also shown that the rate of release of the antibiotic increases with the proportion of antibiotic contained in the powder. It is thus possible, for a powder having given mean sizes, to choose the concentration of the antibiotic so as to obtain a suitable rate of release. For example, a powder will be chosen having a proportion of antibiotic sufficient for the amount of antibiotic released, in an isotonic phosphate buffer of pH 7.4 at 37° C., after 24 hours, to be at least equal to 20% of the initial amount of antibiotics and to be less than 70% (in particular less than 50%) of the said initial amount.

Generally, in the powders of the invention, the concentration of the antibiotic is between 5 and 30% by weight, and chosen, in particular, depending on the particle sizes of the powder.

Likewise, the liberation studies of the antibiotic in a phosphate buffer have shown that the rate of release of the antibiotic decreases when the molecular mass of the poly(lactic acid) increases.

Thus, by using the model of the liberation of the antibiotic in a phosphate buffer, as indicated above, it is possible easily to determine, by simple routine experiments, the particle sizes of the powders, the antibiotic concentrations in the said powders and the molecular masses of the poly(lactic acid) which will give the desired release profiles of the antibiotic.

As already indicated above, poly(lactic acid) matrices having low molecular masses, in particular less than 10,000, lead to pastes or powders being obtained which release the antibiotic too rapidly to be able to be used on their own. More precisely, in the case of an amine-containing antibiotic, the antibiotic in the salt form gives a paste with the low molecular mass poly(lactic acid), whereas the antibiotic in the non-salt form gives a powder. For example, the low molecular mass poly(lactic acid) described in Example 2 of the experimental part below, in combination with 10% of gentamycin base, gives a powder which, in a phosphate buffer, releases, over 24 hours, approximately 50% of the antibiotic which it contains, and then the level of release of antibiotic is low in the days which follow. Such a powder could not be used on its own but could be used in combination with a powder whose poly(lactic acid) matrix has a molecular mass and/or a particle size sufficient for the release of the antibiotic which it contains to be more progressive.

According to a second embodiment, the composition of the invention is provided in the form of a thin film. It is possible to obtain thin poly(lactic acid) films, which can be used according to the invention, by conventional processes for the manufacture of films, especially by mixing an amorphous poly(lactic acid), of high mean molecular mass, for example greater than 20,000, with an amorphous poly(lactic acid) of low mean molecular mass, in particular less than 5,000, the latter acting as plasticizing agent. The proportion of poly(lactic) acid of low molecular mass could, in particular, be a proportion sufficient for the glass transition temperature of the mixture of polymers to be less than a predetermined temperature, for example 37° C. In fact, the glass transition temperature decreases when the proportion of polymer of low molecular mass increases.

The implantable thin films of the invention are, of course, flexible films (or ones capable of rapidly being converted to flexible films on contact with the body fluids present at the site of implantation), so as to prevent traumatism of the tissues and to adapt to the shape of the surgical site.

It is possible easily to adjust the flexibility of the film, which increases with the content of poly(lactic acid) of low molecular mass.

It is recalled that poly(lactic acid)s having low molecular masses are commercially available. Amorphous poly(lactic acid)s of low molecular mass can also be obtained according to known methods, in particular by polycondensation of mixtures of L- and D-lactic acids, for example of D,L-lactic acid.

The liberation studies of the antibiotic (in a phosphate buffer, as indicated above) from films have shown that, as for the powders, the rate of release of the antibiotic increases when the proportion of the antibiotic increases.

These studies have also shown that the rate of release of the antibiotic increases when the proportion of poly(lactic acid) of low molecular mass increases.

It is thus possible to adjust, by simple routine experiments, the suitable proportions of poly(lactic acid) of low molecular mass and/or of antibiotic to obtain the desired rate of release of antibiotic.

Generally, the proportion of poly(lactic acid) of low molecular mass in the mixture of polymers will be between 1 and 50% by weight, and in particular between 5 and 40%.

For a given mixture of polymers, a proportion of antibiotic will be chosen, for example, which is sufficiently high for the amount of antibiotic released, in an isotonic phosphate buffer of pH 7.4 at 37° C., at the end of 24 hours, to be at least equal to 20% of the initial amount, for a film having an initial thickness of 0.3 mm, the said proportion of antibiotic being chosen which is sufficiently low for the said amount released to be less than 70% of the initial amount.

It is also, or simultaneously, possible to act on the proportions of the polymers and to choose a proportion of polymer of low molecular mass which is both sufficiently high and sufficiently low for the amount of antibiotic released, under the conditions which have just been indicated, to lie in the range already mentioned.

To prepare a composition in the film form, it is possible to proceed as in the case of the powders, that is to say to mix the particles of antibiotic and the poly(lactic acid) in a solvent of the polymer in which the antibiotic is insoluble and then to evaporate the solvent, preferably slowly so as to avoid formation of surface bubbles. The poly(lactic acid) is here the mixture of polymers of high molecular mass and of low molecular mass. The thickness of the film can then be adjusted by calendering. It is also possible to mix the antibiotic particles by kneading with the polymer and then to form a film by calendering.

Films are thus prepared having, for example, a thickness which can vary in the range of 0.05–1 mm.

To promote chemical exchanges, healing of the tissues and blood circulation (revascularization) at the site of implantation, it is possible to convert the film into a perforated film, furnished with a plurality of perforations. The surface area of the perforations represents, for example, from 10 to 70% of the total surface area of the film, depending on the thickness of the film. The surface area of the perforations can become larger as the film becomes thicker.

The antibiotic present in the compositions of the invention is preferably a broad-spectrum antibiotic. It is, however, possible to combine a number of antibiotics, not only antibacterial but also antifungal. Of course, antibiotics will preferably be chosen which are not, or rarely, allergizing. Mention may for example be made of aminoglycosides such as gentamycin, tobramycin, amikacin, netilmicin or neomycin; macrolides such as erythromycin; polypeptide antibiotics such as polymyxin B, bacitracin or gramicidin; lincomycin and its derivatives, especially clindamycin; rifamycins, in particular rifampicin; tetracyclines; 5-nitroimidazoles such as metronidazole and tinidazole; ketoconazole, nystatin, griseofulvin, amphotericin; or also fusidic acid (in the soluble salt form), spectinomycin or vancomycin.

The antibiotics often contain amine groups which can form salts. The antibiotic present in the composition of the invention can be in the free form or the salt form. The salts are, of course, salts which are compatible with a pharmaceutical use. Mention will for example be made of, the sulphates, the hydrochlorides and the like, or also salts obtained with polyanions, preferably bioresorbable ones, such as the poly(malic acid) which is described especially in U.S. Pat. Nos. 4,265,247 and 4,320,753. Likewise, antibiotics containing carboxyl groups can be used in the form of salts, for example of alkali metal (sodium, potassium) salts.

It should be noted that when an amine-containing antibiotic is not in the salt form, it can combine with the carboxyl groups of the poly(lactic acid) (end carboxyl groups or carboxyl groups appearing as a result of the degradation of the polyacid). Generally, such a combination will have a tendency to reduce the rate of release of the antibiotic and/or to restrict this release.

Another subject of the invention is a process of therapeutic treatment intended to implement a postsurgical local internal antibiotherapy, characterized in that there is implanted, in the operating cavity, an effective amount of a composition in the ground powder or thin film form, as defined above.

The composition of the invention is administered as indicated above, especially in man, by implanting at the end of the surgical operation, before suturing the wound. The doses used are those which make it possible to obtain release of the antibiotic at effective doses, these effective doses being known. It is thus possible to determine, in each case, the doses of implantable composition which it is advisable to use (for example using the phosphate buffer study model mentioned above).

Of course, it is possible to combine the use of a composition in the powder form with a composition in the film form, the composition in the powder form being chosen, for example, to make possible faster release of the antibiotic in the first hours following the implantation.

The following examples illustrate the invention without, however, limiting it.

EXAMPLE 1

Preparation of ground powders

A lactic acid polymer is prepared by polymerization of D,L-lactide. For this, a bulk polymerization is carried out, in the presence of 0.05% by weight of zinc, in a sealed round-bottomed flask at 140° C. with stirring, for 3 weeks After cooling, the reaction product is dissolved in chloroform or acetone and an alcohol (methanol or ethanol) is added to precipitate the polymer formed, while the residual monomers and the poly(lactic acid)s of low molecular weight formed remain in solution. The polymer is then dried for one week under vacuum at 40° C.

The polymer obtained has a number-average molecular mass of 160,000 and a weight-average molecular mass of 280,000.

The X-ray diffraction spectrum shows the absence of crystalline domains.

This amorphous polymer has a glass transition temperature, determined by differential thermal analysis, of approximately 44° C.

5 g of this polymer are dissolved in 100 ml of acetone. An amount of gentamycin sulphate is added which is sufficient for the final mixture to have a gentamycin sulphate content of 10% by weight. The mixture is then evaporated to dryness using a rotary evaporator and is then dried under reduced pressure at 40° C.

The dried product is then cryogenically ground (at the temperature of liquid nitrogen). After grinding, it is in the form of solid particles. Three fractions, having particle sizes respectively between 0.125–0.25 mm (small sizes), 0.25–0.5 mm (medium sizes) and 0.5–1 mm (large sizes), are separated by sieving.

The studies of the liberation of the antibiotic in a phosphate buffer, under the conditions indicated above, show that the powders of small size release more than 50% of the antibiotic which they contain in 24 hours. The release is then very low. The powders of average size release approximately 40% of the antibiotic in 24 hours and approximately 55% in the first ten days. Particles of large size release 25 to 30% of the antibiotic on the first day, to reach a release of 50% at the end of 10 days.

Powders containing respectively 20% and 30% of gentamycin sulphate were prepared analogously, as well as powders containing one of the following antibiotics: tobramycin, neomycin, bacitracin, clindamycin and rifampicin.

A powder containing 20% by weight of a poly(malic acid) and gentamycin complex was also analogously prepared, this complex having been prepared from the sodium salt of a poly(malic acid) (MM: 20,000) dissolved in water, to which an excess of gentamycin sulphate is added.

EXAMPLE 2

Preparation of films

A poly(lactic acid) was prepared in a way analogous to that described in Example 1, with the following characteristics:

$M_n$=170,000

$M_w$=280,000

Glass transition temperature: 35° C.

Absence of crystalline domains.

Moreover, a poly(lactic acid) of low molecular weight was prepared by polycondensation of D,L-lactic acid at 140° C. under vacuum for 3 days. After cooling, the reaction product is dissolved in acetone and the polymer is precipitated by addition of water to the solution, while the residual monomers remain in solution. The polymer is then dried for one week under vacuum.

It has the following characteristics:

$M_n$=2,000

$M_w$=2,600

This polymer is in the form of a viscous and sticky paste. Its glass transition temperature is of the order of 0° C.

As in Example 1, the polymers, in suitable proportions, are dissolved in acetone and a calculated amount of gentamycin sulphate is added. The mixture is then run into a Petri dish coated with Teflon.

The solvent is evaporated at room temperature, under atmospheric pressure, to prevent the formation of surface bubbles. Drying is then completed under reduced pressure. Finally, calendering is carried out with a calender containing chromium-plated rollers.

Films were thus prepared having a thickness of approximately 0.3 mm in which the proportion of poly(lactic acid) of low molecular mass is 10, 20 or 30% with respect to the total mass of the polymers, these films containing, by weight, 10% or 20% of gentamycin sulphate.

Films were analogously prepared in which the polymer of low molecular mass is a polymer obtained by polycondensation of a mixture of D-lactic and L-lactic acids containing 70% of D-lactic acid.

The studies of the liberation in a phosphate buffer show that the "burst" phenomenon is reduced in the case of films. At the end of 24 hours, approximately 20% of the antibiotic is released in the case of a matrix containing 10% or 20% of polymer of low molecular mass, for the films containing 10% of gentamycin sulphate. The release of the antibiotic then continues steadily, being faster as the content of polymer of low molecular mass is higher. In the case of the matrix containing 20% of polymer of low molecular mass, the release of the antibiotic reaches 50% between approximately 20 and 30 days.

Films were analogously prepared containing one of the following antibiotics: oxytetracycline, doxycycline, erythromycin, metronidazole, ketoconazole, clindamycin and chloramphenicol.

EXAMPLE 3

In vivo study

Implantation of particles

Particles having sizes between 0.5 and 1 mm, containing 10% of gentamycin sulphate, obtained in Example 1, were implanted in the posterior part of the paravertebral muscle of rabbits at two implantation sites per animal, on each side of the vertebral column. The amounts implanted were 100 mg.

The amount of gentamycin excreted in the urine is regularly quantitatively determined, according to a method analogous to that described by Gambardella et al., Journal of Chromatography, 348, 229–240 (1985).

The amount excreted is large on the first two days (respectively 2 and 3 mg/day on the first and second days) and then decreases slowly until the fifteenth day after implantation.

At the end of 14 days, a small region of necrosis of the muscle tissues is generally observed at the sites of implantation.

By comparison, gentamycin sulphate implanted alone (10 mg) gives extensive regions of necrosis; urinary excretion is very high on the first day (7 mg/day), decreases to 1 mg/day on the second day and becomes zero on the eighth day.

Implantation of films

The films were implanted, as above, in rabbits, at 75 mg per site of implantation.

The films used, obtained as described in Example 2, are mixtures of polymers containing respectively 10%, 20% or 30% of the poly(D,L-lactic acid) of low molecular mass, all the films studied containing 10% of gentamycin sulphate.

This study lasted 10 days.

As in the case of powders, urinary excretion of gentamycin is high on the first two days and then decreases on the following days. It is still present after 10 days whereas, with gentamycin sulphate implanted alone, it becomes virtually zero on the seventh day. Moreover, the amounts of antibiotic excreted become larger as the proportion of polymer of low molecular mass increases.

On the tenth day, necroses are markedly greater in rabbits which have received gentamycin sulphate alone. Additionally, it is noticed that the thickness of the necrosed regions around the implants is approximately half that of the necrosed regions of the implantation channel, which suggest that the necrosis is essentially due to surgical traumatism during insertion of the films.

In conclusion, the in vivo studies have shown, with the implantable compositions of the invention, the progressive release of the antibiotic after a more or less strong burst, depending in particular on the nature of the implant.

In vivo studies have generally confirmed the validity of the results obtained with the in vitro release model in a phosphate buffer.

The toxicity is less than with gentamycin sulphate implanted alone, and the tissue reactions are relatively weak, which confirms the excellent biocompatibility of the implantable compositions of the invention.

We claim:

1. A bioresorbable pharmaceutical composition comprising poly(lactic acid), said composition being implantable so as to implement a local internal antibiotherapy for those in need thereof, said composition comprising an antibiotically effective amount of at least one water-soluble antibiotic in the form of particles of controlled size less than 100 µm dispersed homogeneously in a poly(lactic acid) matrix, said composition being provided in the form of (i) either a ground powder obtained by grinding a homogeneous dispersion of said antibiotic in an amorphous poly(lactic acid) matrix having a mean molecular mass ranging from 10,000 to 300,000 or (ii) a thin film whose poly(lactic acid) matrix is made of a mixture of (1) an amorphous poly(lactic acid) having a mean molecular mass greater than 20,000 and (2) an amorphous poly(lactic acid) having a mean molecular mass less than 5,000.

2. The pharmaceutical composition of claim 1 wherein said amorphous poly(lactic acid) matrix comprises a mixture of units derived from a D- and L-lactic acid, the amount of each of said D- and L-units being sufficient for said poly-(lactic acid) to be amorphous.

3. The pharmaceutical composition of claim 2 wherein said poly(lactic acid) contains from 20 to 80 percent of D-lactic units.

4. The pharmaceutical composition of claim 3 wherein said poly(lactic acid) contains units derived from D- and L-lactic acids in equal proportions.

5. The pharmaceutical composition of claim 1 in the form of a ground powder wherein said amorphous poly(lactic acid) matrix has a molecular mass at least equal to 10,000.

6. The pharmaceutical composition of claim 1 in the form of a ground powder wherein said amorphous poly(lactic acid) matrix has a molecular mass ranging from 10,000 to 30,000.

7. The pharmaceutical composition of claim 1 wherein said ground powder has a particle size ranging from 0.1 to 1 mm.

8. The pharmaceutical composition of claim 7 wherein said ground powder comprises a mixture of (a) particles having a size ranging from 0.1 to 0.2 mm and (b) particles having a size ranging from 0.5 to 1 mm.

9. The pharmaceutical composition of claim 8 wherein the concentration of said antibiotic is sufficient for the amount of antibiotic released, in an isotonic phosphate buffer of pH 7.4 at 37° C., at the end of 24 hours, to be at least equal to 20 percent of the initial amount of antibiotic and less than 70 percent of the initial amount.

10. The pharmaceutical composition of claim 9 wherein the amount of said antibiotic ranges from 5 and 30 percent by weight.

11. The pharmaceutical composition of claim 1 wherein the amount of said amorphous poly(lactic acid) having a molecular mass less than 5,000 is sufficient for a glass transition of said mixture of polymers being less than 37° C.

12. The pharmaceutical composition of claim 1 wherein the amount of the water-soluble antibiotic or the low molecular mass poly(lactic acid) or mixture thereof is sufficiently high for the amount of antibiotic released, in an isotonic phosphate buffer of pH 7.4, at 37° C., at the end of 24 hours, to be as least equal to 20 percent of the initial amount, for a film having an initial thickness of 0.3 mm, and wherein said amounts are sufficiently low for said amount released being less than 70 percent of the initial amount.

13. The pharmaceutical composition of claim 1 wherein said film has a thickness in the range of 0.05–1 mm.

14. The pharmaceutical composition of claim 1 wherein said film is provided with a plurality of perforations.

15. The pharmaceutical composition of claim 14 wherein the surface area of said perforations represents from 10 to 70 percent of the total surface area of said film.

16. The pharmaceutical composition of claim 1 wherein said water-soluble antibiotic in the form of particles have a size ranging from 0.01 to 50 µm.

17. The pharmaceutical composition of claim 1 wherein said antibiotic is present in the form of a pharmaceutically acceptable salt.

18. A process for preparing an implantable and bioresorbable pharmaceutical composition in the form of a powder, said composition comprising poly(lactic acid) and an antibiotically effective amount of at least one water-soluble antibiotic in the form of particles of controlled size less than 100 µm, said antibiotic being dispersed homogeneously in an amorphous poly(lactic acid) matrix, said process comprising grinding a homogeneous dispersion of said antibiotic in said amorphous poly(lactic acid) matrix having a molecular mass ranging from 10,000 to 300,000.

19. A process for preparing an implantable and bioresorbable pharmaceutical composition in the form of a thin film, said composition comprising poly (lactic acid) and at least one water-soluble antibiotic in the form of particles of controlled size less than 100 µm, said antibiotic being dispersed homogeneously in an amorphous poly(lactic acid) matrix, said process comprising admixing said amorphous poly(lactic acid) having a molecular mass greater than 20,000 with an amorphous poly(lactic acid) having a molecular mass less than 5,000.

20. The process of claim 19 further comprising mixing said water-soluble antibiotic particles and said amorphous poly(lactic acid) matrix in a solvent of a polymer wherein said antibiotic is insoluble, said solvent being evaporated and the resulting composition being ground or calendered.

21. The process of claim 20 wherein said mixing comprises kneading said at least one water-soluble antibiotic in the form of particles with said amorphous poly(lactic acid) to produce a film, and calendering said film.

\* \* \* \* \*